US006492166B1

(12) United States Patent
Ferris et al.

(10) Patent No.: US 6,492,166 B1
(45) Date of Patent: Dec. 10, 2002

(54) USE OF CONSTITUTIVE TRANSPORT ELEMENTS FOR HOST RANGE CONTROL

(75) Inventors: Andrea L. Ferris, Frederick, MD (US); Stephen H. Hughes, Smithsburg, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/744,022

(22) PCT Filed: Jul. 28, 1999

(86) PCT No.: PCT/US99/17086

§ 371 (c)(1), (2), (4) Date: Jan. 19, 2001

(87) PCT Pub. No.: WO00/06760

PCT Pub. Date: Feb. 10, 2000

Related U.S. Application Data

(60) Provisional application No. 60/094,535, filed on Jul. 29, 1998.

(51) Int. Cl.[7] ........................ C12N 15/74; C12N 15/63; C12N 15/85; C12N 15/87; C12N 15/86

(52) U.S. Cl. .................... 435/320.1; 435/455; 435/456; 536/23.1

(58) Field of Search ...................... 536/23.1; 435/320.1, 435/455, 456

(56) References Cited

U.S. PATENT DOCUMENTS

| | | | |
|---|---|---|---|
| 5,043,270 A | | 8/1991 | Abrams et al. |
| 5,585,263 A | | 12/1996 | Hammarskjöld et al. |
| 5,650,306 A | * | 7/1997 | Nabel et al. |
| 5,681,746 A | | 10/1997 | Bodner et al. |
| 5,736,388 A | | 4/1998 | Chada et al. |
| 5,770,428 A | | 6/1998 | Boris-Lawrie |
| 5,880,276 A | | 3/1999 | Hammarskjöld et al. |

FOREIGN PATENT DOCUMENTS

| | | | |
|---|---|---|---|
| EP | 0 334 301 A1 | | 9/1989 |
| EP | 0 611 822 A2 | | 2/1994 |
| WO | 0611822 A2 | * | 5/1994 |
| WO | WO 96/37625 | | 11/1996 |
| WO | WO 99/04026 | | 1/1999 |

OTHER PUBLICATIONS

Holland et al. Enhancer sequences of a retroviral vector determine expression of a gene in multipotent hematopoietic and committed eryrhroid cells vol. 84. pp. 8662–8666 Dec. 1987 Medicine Sciences.*

Bray et al., "A Small Element from the Mason–Pfizer Monkey Virus Genome Makes Human Immunodeficiency Virus Type 1 Expression and Replication Rev–Independent," *Proc. Natl. Acad. Sci. USA 91*:1256–1260 (1994).

Hughes et al., "Mutagenesis of the Region Between env and src of the SR–A Strain of Rous Sarcoma Virus for the Purpose of Constructing Helper–Independent Vectors," *Virology 136*:89–99 (1984).

Nasiouslas et al., "Production of Avian Leukosis Virus Particles in Mammalian Cells Can be Mediated by the Interaction of the Human Immunodeficiency Virus Protein Rev and the Rev–Responsive Element," *Proc. Natl. Acad. Sci. USA 92*:11940–11944 (1995).

Ogert et al., "Avian Retroviral RNA Element Promotes Unspliced RNA Accumulation in the Cytoplasm," *J. Virol. 70*:3834–3843 (1996).

Ott et al., "Phenotypes of Murine Leukemia Virus–Induced Tumors: Influence of 3' Viral Coding Sequences," *J. Virology 66*:6107–6116 (1992).

Pasquinelli et al., "The Constitutive Transport Element (CTE) of Mason–Pfizer Monkey Virus (MPMV) Accesses a Cellular mRNA Export Pathway," *EMBO J. 16*:7500–7510 (1997).

Petropoulos et al., "Replication–Competent Retrovirus Vectors for the Transfer and Expression of Gene Cassettes in Avian Cells," *J. Virology 65*:3728–3737 (1991).

Rizvi et al., "Role of Mason–Pfizer Monkey Virus (MPMV) Constitutive Transport Element (CTE) in the Propagation of MPMV Vectors by Genetic Complementation Using Homologous/Heterologous env Genes," *Virology 224*:517–532 (1996).

Saavedra et al., "The Simian Retrovirus–1 Constitutive Transport Element, Unlike the HIV–1 RRE, Uses Factors Required for Cellular mRNA Export," *Curr. Biol. 7*:619–628 (1997).

Shinnick et al., "Nucleotide Sequence of Moloney Murine Leukaemia Virus," *Nature 293*:543–548 (1981).

Sorge et al., "cis–Acting RNA Packaging Locus in the 115–Nucleotide Direct Repeat of Rous Sarcoma Virus," *J. Virology 48*:667–675 (1983).

Tang et al., "Identification and Purification of Cellular Proteins that Specifically Interact with the RNA Constitutive Transport Elements from Retrovirus D," *Virology 228*:333–339 (1997).

(List continued on next page.)

*Primary Examiner*—Remy Yucel
*Assistant Examiner*—Konstantina Katcheves
(74) *Attorney, Agent, or Firm*—Klarquist Sparkman, LLP

(57) ABSTRACT

An Avian-derived retroviral vector from which the Constitutive Transport Element (CTE) has been removed and replaced with a genetic fragment from a mammalian virus in order to produce a vector that is replication competent in at least one non-native cell type without the need for a "helper" virus, and that is unlikely to recombine with endogenous mammalian viruses, making it both safe and simple to use in research and gene-therapy applications.

13 Claims, 3 Drawing Sheets

OTHER PUBLICATIONS

Whitcomb et al., "Repliclation of Avian Leukosis Viruses with Mutations at the Primer Binding Site: Use of Alternative tRNAs as Primers," *J. Virology 69*:6228–6238 (1995).

Yin et al., "Insertion of Sequences into the 3' Untranslated Region of a Replication–Competent Spleen Necrosis Virus Vector Disrupts env Gene Expression," *Arch. Virol. 144*:73–87 (1999).

Zolotukhin et al., "Continuous Propagation of RRE(–) and Rev(–)RRE(–) Human Immunodeficiency Virus Type 1 Molecular Clones Containing a cis–Acting Element of Simian Retrovirus Type 1 in Human Peripheral Blood Lymphocytes," *J. Virology 68*:7944–7952 (1994).

* cited by examiner

```
         10        20        30        40        50        60        70        80        90
ATGTTTCCAGGGTGCCCCAAGGACCTGAAATGACCCTGTGCCTTATTTGAACTAACCAATCAGTTCGCTTCTCGCTTCTGTTCGCGCGCTTCTGCT
TACAAAGGTCCCACGGGGTTCCTGGACTTTACTGGGACACGGAATAAACTTGATTGGTTAGTCAAGCGAAGAGCGAAGACAAGCGCGCGAAGACGA
```

FIGURE 1

```
         10        20        30        40        50        60        70        80        90
AGCTGAATATGGGCCAAACAGGATATCTGTGGTAAGCAGTTCCTGCCCCGGCTCAGGGCCAAGAACAGATGGTCCCCAGATGCGGTCCAGCCCTCAG
TCGACTTATACCCGGTTTGTCCTATAGACACCATTCGTCAAGGACGGGGCCGAGTCCCGGTTCTTGTCTACCAGGGGTCTACGCCAGGTCGGGAGTC

  100       110       120       130       140       150       160       170       180       190
CAGTTTCTAGAGAACCATCAGATGTTTCCAGGGTGCCCCAAGGACCTGAAATGACCCTGTGCCTTATTTGAACTAACCAATCAGTTCGCTTCTCGCT
GTCAAAGATCTCTTGGTAGTCTACAAAGGTCCCACGGGGTTCCTGGACTTTACTGGGACACGGAATAAACTTGATTGGTTAGTCAAGCGAAGAGCGA

     200       210       220
TCTGTTCGCGCGCTTCTGCTCCCCGA
AGACAAGCGCGCGAAGACGAGGGGCT
```

FIGURE 2

```
        10        20        30        40        50        60        70        80        90
ATAAAATAAAAGATTTTATTTAGTCTCCAGAAAAAGGGGGGAATGAAAGACCCCACCTGTAGGTTTGGCAAGCTAGCTTAAGTAACGCCATTTTGCA
TATTTTATTTTCTAAAATAAATCAGAGGTCTTTTTCCCCCCTTACTTTCTGGGGTGGACATCCAAACCGTTCGATCGAATTCATTGCGGTAAAACGT

   100       110       120       130       140       150       160       170       180       190
AGGCATGGAAAAATACATAACTGAGAATAGAGAAGTTCAGATCAAGGTCAGGAACAGATGGAACAGCTGAATATGGGCCAAACAGGATATCTGTGGT
TCCGTACCTTTTTATGTATTGACTCTTATCTCTTCAAGTCTAGTTCCAGTCCTTGTCTACCTTGTCGACTTATACCCGGTTTGTCCTATAGACACCA

      200       210       220       230   236 240       250       260       270       280       290
AAGCAGTTCCTGCCCCGGCTCAGGGCCAAGAACAGATGGAACAGCTGAATATGGGCCAAACAGGATATCTGTGGTAAGCAGTTCCTGCCCCGGCTCA
TTCGTCAAGGACGGGGCCGAGTCCCGGTTCTTGTCTACCTTGTCGACTTATACCCGGTTTGTCCTATAGACACCATTCGTCAAGGACGGGGCCGAGT

         300       310       320       330       340       350 354   360       370       380
GGGCCAAGAACAGATGGTCCCCAGATGCGGTCCAGCCCTCAGCAGTTTCTAGAGAACCATCAGATGTTTCCAGGGTGCCCCAAGGACCTGAAATGAC
CCCGGTTCTTGTCTACCAGGGGTCTACGCCAGGTCGGGAGTCGTCAAAGATCTCTTGGTAGTCTACAAAGGTCCCACGGGGTTCCTGGACTTTACTG

  390       400       410       420       430      439         450 455  460       470       480
CCTGTGCCTTATTTGAACTAACCAATCAGTTCGCTTCTCGCTTCTGTTCGCGCGCTTCTGCTCCCCGAGCTCAATAAAAGAGCCCACAACCCCTCAC
GGACACGGAATAAACTTGATTGGTTAGTCAAGCGAAGAGCGAAGACAAGCGCGCGAAGACGAGGGGCTCGAGTTATTTTCTCGGGTGTTGGGGAGTG

     490       500       510       520       530       540       550       560       570       580
TCGGGGCGCCAGTCCTCCGATTGACTGAGTCGCCCGGGTACCCGTGTATCCAATAAACCCTGCGCCAGTCCTCCGATTGACTGAGTCGCCCGGGTAC
AGCCCCGCGGTCAGGAGGCTAACTGACTCAGCGGGCCCATGGGCACATAGGTTATTTGGGACGCGGTCAGGAGGCTAACTGACTCAGCGGGCCCATG

        590       600       610
CCGTGTATCCAATAAACCCTCTTGCAGTTGCA
GGCACATAGGTTATTTGGGAGAACGTCAACGT
```

FIGURE 3

SEQUENCE LISTING

<160> NUMBER OF SEQ ID NOS: 9

<210> SEQ ID NO 1
<211> LENGTH: 96
<212> TYPE: DNA
<213> ORGANISM: Moloney murine leukaemia virus

<400> SEQUENCE: 1

```
atgtttccag ggtgccccaa ggacctgaaa tgaccctgtg ccttatttga actaaccaat     60

cagttcgctt ctcgcttctg ttcgcgcgct tctgct                               96
```

<210> SEQ ID NO 2
<211> LENGTH: 220
<212> TYPE: DNA
<213> ORGANISM: Moloney murine leukaemia virus

<400> SEQUENCE: 2

```
agctgaatat gggccaaaca ggatatctgt ggtaagcagt tcctgccccg gctcagggcc     60

aagaacagat ggtccccaga tgcggtccag ccctcagcag tttctagaga accatcagat    120

gtttccaggg tgccccaagg acctgaaatg accctgtgcc ttatttgaac taaccaatca    180

gttcgcttct cgcttctgtt cgcgcgcttc tgctccccga                          220
```

<210> SEQ ID NO 3
<211> LENGTH: 703
<212> TYPE: DNA
<213> ORGANISM: Moloney murine leukaemia virus

<400> SEQUENCE: 3

```
ataaaataaa agattttatt tagtctccag aaaaaggggg gaatgaaaga ccccacctgt     60

aggtttggca agctagctta agtaacgcca ttttgcaagg catggaaaaa tacataactg    120

agaatagaga agttcagatc aaggtcagga acagatggaa cagctgaata tgggccaaac    180

aggatatctg tggtaagcag ttcctgcccc ggctcagggc caagaacaga tggaacagct    240

gaatatgggc caaacaggat atctgtggta agcagttcct gccccggctc agggccaaga    300

acagatggtc cccagatgcg gtccagccct cagcagtttc tagagaacca tcagatgttt    360

ccagggtgcc ccaaggacct gaaatgaccc tgtgccttat ttgaactaac caatcagttc    420

gcttctcgct tctgttcgcg cgcttctgct ccccgagctc aataaaagag cccacaaccc    480

ctcactcggg gcgccagtcc tccgattgac tgagtcgccc gggtacccgt gtatccaata    540

aaccctgcgc cagtcctccg attgactgag tcgcccgggt acagccccgc ggtcaggagg    600

ctaactgact cagcgggccc atgggcacat aggttatttg ggacgcggtc aggaggctaa    660

ctgactcagc gccgtgtatc caataaaccc tcttgcagtt gca                      703
```

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 4

```
atgtttccag ggtgccccaa                                                 20
```

<210> SEQ ID NO 5
<211> LENGTH: 21

-continued

```
<212> TYPE: DNA
<213> ORGANISM: Artificial Sequence
<220> FEATURE:
<223> OTHER INFORMATION: Description of Artificial Sequence: PCR primer

<400> SEQUENCE: 5

agcagaagcg cgcgaacaga a                                              21


<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 6

gagctgactc tgctggtgcc                                                20


<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 7

ccccctccct atgcaaaagc g                                              21


<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 8

agctgaatat gggccaaaca                                                20


<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 9

tcggggagca gaagcgcgcg                                                20
```

USE OF CONSTITUTIVE TRANSPORT ELEMENTS FOR HOST RANGE CONTROL

PRIORITY CLAIM

This is a U.S. National Stage §371 of PCT/US99/17086, filed Jul. 28, 1999, which was published in English under PCT Article 21(2), which claims the benefit of U.S. Provisional Application 60/094,535, filed Jul. 29, 1998.

FIELD OF THE INVENTION

The present invention relates to retroviral vectors that are useful in laboratory research and clinical therapy.

BACKGROUND

In retroviruses, both spliced and unspliced retroviral RNAs must be efficiently transported from the nucleus to the cytoplasm. In simple retroviruses, like the Avian Sarcoma Leukosis Viruses (ASLV) and Murine Leukemia Virus (MLV) (Coffin et al., 1997, pg. 75–77), RNAs contain a specialized structure called a Constitutive Transport Element (CTE). The CTE is recognized by cellular factors and aids in nuclear export of unspliced viral RNAs so that they may be correctly expressed and packaged. This process is necessary for assembly and production of replication competent viruses. Because of their role in nuclear transport, CTEs play a role in determining the host-range of some viruses. For example, ASLV cannot successfully replicate in mammalian cells, in part, because the ASLV CTE is not fully functional in mammalian cells. This is thought to be because the avian CTE is not recognized by mammalian cellular factors.

CTEs of both avian and mammalian retroviruses have been previously described. Bray et al. (1994) teaches a 219 nucleotide element in the 3' untranslated region of the genome of Mason-Pfizer Monkey Virus (MPMV) (located between the env gene and the 3' LTR) that can functionally substitute for the Rev protein and its RRE sequence in promoting transport of unspliced HIV RNAs. Nasioulas et al. (1995), teaches that the HIV 1 Rev/RRE system can increase the expression of Avian Leukosis Virus (ALV) structural proteins in mammalian cells and promote the release of mature ALV from these cells, demonstrating that ALV viral replication is dependent on appropriate post-transcriptional RNA regulation. Ogert et al. (1996), teaches an avian retroviral RNA element that promotes unspliced RNA accumulation in the cytoplasm and thereby promotes Rev-independent expression of HIV protein.

Prior researchers have extended the host range of retroviral vectors by the manipulation of envelope proteins. U.S. Pat. No. 5,591,624 and U.S. Pat. No. 5,716,832, teach the production of recombinant retroviruses adapted to infect a particular cell type, such as a tumor, by manipulating the binding specificity of those retroviruses. U.S. Pat. No. 5,512,421 discloses manipulation of the host-range of retroviral vectors by alteration of the retroviral envelope protein so that the vector may infect a wide-range of non-mammalian cells. Barsov and Hughes (1996) discloses the manipulation of host-range of a Rous Sarcoma Virus (RSV) derived vector by the substitution of the avian env gene with a mammalian env gene.

Heterologous genes have been previously expressed in retroviral vectors. U.S. Pat. No. 5,252,465 teaches the expression of heterologous genes in avian erythroblastosis virus vectors. U.S. Pat. No. 5,652,130 discloses the use of retroviral vectors for expressing Tumor Necrosis Factor (TNF). U.S. Pat. No. 5,635,399 teaches retroviral vectors expressing cytokine genes in retroviral vectors. Barsov and Hughes (1996) teaches the expression of MLV env in a Rous Sarcoma Virus derived vector.

Constitutive Transport Elements (CTEs) are parts of the retroviral RNA genome that play a role in post transcriptional regulation of unspliced RNAs. Rizvi et al. (1996) discloses that the CTE of Mason-Pfizer Monkey Virus (MPMV) is a cis-acting element critical for the replication of MPMV. Rizvi concludes that the CTE facilitates the transport of viral mRNA from the nucleus in a similar manner to the Rev/RRE system of HIV and SIV. Rizvi found that without the CTE there was a six-fold increase in MPMV RNA sequestered in the nucleus compared with the cytoplasm.

Other researchers have taught that the CTE of MPMV is a cis-acting element that promotes nuclear export of mRNAs (Pasquinelli et al., 1997). In U.S. Pat. No. 5,585,263 a cis-acting retroviral mRNA "constitutive enhancer element" is described that promotes transport of intron-containing mRNA and, in conjunction with certain proteins, provides for rev-independent expression of certain HIV genes.

Retroviral vectors are widely used in laboratory research and may be used for clinical gene therapy. The currently used retroviral vectors, however, have certain inherent disadvantages. Mammalian retroviral vectors can recombine with other endogenous mammalian viruses, which poses obvious clinical dangers (and regulatory approval problems) in gene therapy. Also, the presently used retroviruses commonly require a "helper" virus for successful infection and replication, making them difficult to use. Moreover, currently used vectors have restricted host-ranges and replicate only, for instance, in mammalian cells or only in avian cells; the host range of these vectors cannot at present, be easily manipulated.

There is a need for a retroviral vector that reduces the probability of recombination with endogenous mammalian viruses, that needs no "helper" virus or special cell line, and that can be easily manipulated with respect to host range. There is also a need for a method by which a user may manipulate the host range of a selected vector. Such a retroviral vector would be more useful, easier to use, and more flexible than current retroviral vectors, both in the laboratory and in clinical gene therapy applications.

SUMMARY OF THE DISCLOSURE

The present invention provides a retroviral vector wherein the constitutive transport element (CTE) has been removed and replaced with a genetic fragment derived from a different species. In particular embodiments, the retroviral vector is an avian retroviral vector from which the CTE has been removed and replaced with a genetic fragment from a mammalian retrovirus. The mammalian fragment performs essentially the function of a CTE allowing the recombinant virus to replicate in at least one non-native type of cell. A fragment that performs such a function is said to be a "CTE-like sequence" and is referred to as being functionally "complementary" to the deleted CTE sequence.

Surprisingly, it has been found that sequences derived from the Long Terminal Repeat (LTR) of the Murine Leukemia Virus (MLV) functionally complement a CTE-deleted avian retrovirus, conferring replication competence in both mammalian and avian cells. Although the genomes of mammalian viruses are believed to contain CTE sequences, the sequences from the LTR of MLV bears no sequence homology to any known CTE sequence, therefore it was unexpected to find that this sequence conferred replication competence upon a CTE-deleted avian virus. The vector of the invention is able to replicate in non-native cell types without the need for a "helper" virus or special cell line, and so is said to be "replication competent" in these non-native cell types.

The current invention enables a researcher or clinician to control the host-range of the retroviral vector by choosing a genetic element with which to substitute the deleted native CTE. For instance, by choosing a complementary genetic element that functions as a CTE only in mammalian cells, the operator can make the engineered avian-derived vector replication competent in mammalian cells but not in other cells. By choosing a genetic element that functions as a CTE in both avian and mammalian cells, the operator can create an avian-derived vector that replicates both in mammalian and avian cells. MLV can be amphotrophic, able to replicate in both avian and mammalian cells, and by replacing the ASLV CTE with a sequence from the LTR of an amphotrophic MLV, the operator can create a broad host-range avian-derived vector. CTE's (and sequences that function essentially as CTE's) may be derived from retroviruses native to many classes and species, such as mammals, birds, amphibians and reptiles.

In one embodiment of the present invention, this mammalian fragment used to complement the deleted avian CTE is derived from the Murine Leukemia Virus Long Terminal Repeat. One embodiment of the present invention is a retroviral vector constructed from RCASBP(A) (Hughes et al., 1990, Petropoulos and Hughes, 1991) that is replication competent in both avian and mammalian cells. RCASBP(A) is an avian retrovirus derived from the Replication Competent ALV with a Splice Acceptor vector (RCAS), which possesses a unique ClaI site into which heterologous polynucleotides may be inserted. The CTE may be removed from RCASBP(A) and replaced by a fragment from the MLV LTR, such as the 96 bp fragment (FIG. 1) or the 220 bp AluI fragment (FIG. 2), or sequences substantially similar to these sequences.

The present invention provides a method for making a broad host-range retroviral vector derived from an avian retroviral vector by wholly or partially removing the CTE and replacing it with a fragment from the genome of a mammalian retrovirus that allows replication in one or more cell types. The present invention also provides a method for using such a vector both for research purposes and for clinical purposes, such as for the delivery of genetic elements, such as genes, into cells by providing the broad host-range vector of the present invention, and by contacting it with a target cell.

Advantages of the present invention include providing a broad host-range retroviral vector which is replication competent in at least one non-native cell type, making it a more flexible research tool than previous retroviral vectors; providing a retroviral vector which requires no "helper" virus for infection or application, making it simpler to use; and providing a retroviral vector which is unlikely to recombine with endogenous mammalian viruses, making it safer to use in human gene therapy.

BRIEF DESCRIPTION OF THE DRAWINGS

FIG. 1, shows the 96 bp nucleic acid sequence of the invention derived from the Long Terminal Repeat of Murine Leukemia Virus (corresponds to SEQ ID NO:1).

FIG. 2, shows the 220 bp AluI fragment nucleic acid sequence of the invention derived from the Long Terminal Repeat of Murine Leukemia Virus (corresponds to SEQ ID NO:2).

FIG. 3, shows the sequence of the LTR of MLV (corresponds to SEQ ID NO:3). The 96 bp sequence of FIG. 1 is located between bases 355 and 450 and the 218 bp sequence of FIG. 2 is located between bases 237 and 456.

SEQUENCE LISTINGS

SEQ ID NO:1 shows the 96 bp nucleic acid sequence of the invention derived from the Long Terminal Repeat of Murine Leukemia Virus.

SEQ ID NO:2 shows the 220 bp AluI fragment nucleic acid sequence of the invention derived from the Long Terminal Repeat of Murine Leukemia Virus.

SEQ ID NO:3 shows the sequence of the LTR of MLV.

SEQ ID NO:4 shows an exemplary forward primer used to amplify the 96 bp polynucleotide (see Example 3).

SEQ ID NO:5 shows an exemplary reverse primer used to amplify the 96 bp polynucleotide (see Example 3).

SEQ ID NO:6 shows an exemplary forward primer used to amplify DNA sequences cloned into the viral ClaI site for clone selection of viruses harboring the 96 bp insert (see Example 4).

SEQ ID NO:7 shows an exemplary reverse primer used to amplify DNA sequences cloned into the viral ClaI site for clone selection of viruses harboring the 96 bp insert (see Example 4).

SEQ ID NO:8 shows an exemplary forward primer used to amplify DNA sequences cloned into the viral ClaI site for clone selection of viruses harboring the 220 bp insert (see Example 4).

SEQ ID NO:9 shows an examplary reverse primer used to amplify DNA sequences cloned into the viral ClaI site for clone selection of viruses harboring the 220 bp insert (see Example 4).

DESCRIPTION OF THE INVENTION

A. DEFINITIONS

A broad host-range virus or vector refers to a virus or vector that is replication competent in cells of more than one type or species, such as a virus or vector that is replication competent in both mammalian and avian cells without the need for a helper virus.

Avian as applied to a virus, refers to any virus that is native to birds. A non-avian virus is any virus that is not native to birds. Mammalian as applied to a virus, refers to any virus that is native to mammals. Avian-derived refers to any cell or virus isolated from a bird. Mammalian derived refers to any cell or virus isolated from a mammal. To say that a virus is replication competent in a non-native cell type means that the virus can replicate in a cell from a Kingdom, Phylum, class, order, family, genus or species that is different from the one in which it is ordinarily found.

A Constitutive Transport Element (CTE), also known as a Constitutive Transport Enhancer, is a viral element that is essential for successful nuclear export of RNA in simple retroviruses (Retroviruses, 1997, Coffin et al eds, see pgs. 235–241, particularly pgs. 238–241). The CTE is typically a cis-acting element found in the 3' untranslated region of the retrovirus genome between the env gene and the 3' LTR (Bray et al., 1994; Zolotukin et al., 1994; Ogert et al., 1996)., and typically has a characteristic stem-loop structure (Rizvi et al., 1996). CTEs are known to complement Rev- REE- mutants of complex viruses (Bray et al., 1994 and Zolotukin et al., 1994). CTEs interact with cellular factors to facilitate transport of unspliced and incompletely spliced viral RNA from the nucleus to the cytoplasm. An example of such a CTE is the 219 bp cis-acting element present in the 3' region of both MPMV and Simian Retrovirus type 1 (SRV-1) (Bray et al., 1994; Zolotukin et al., 1994). This CTE is further described in Genbank file SIVMPCG between nucleotides 8022 and 8240, and is discussed in U.S. Pat. No. 5,585,263, e.g., at column 6. Computer analysis of the MPMV CTE RNA has revealed a stable secondary structure containing three stem-loop structures, the first of which contains a nine nucleotide motif showing a 67% homology to the Rev-binding domain of HIV-1 RRE. Mutations that disrupt this secondary structure drastically affect CTE function (Rizvi et al., 1996). CTEs are found in simple, but not complex retroviruses. In complex ("MC-type") retroviruses (Nasioulas, et al., 1995) such as HIV-1 and SIV, the Rev protein interacts with the Rev-responsive element (RRE), which is a short cis-acting sequence on the viral transcript. The Rev/RRE complex then interacts with cellular factors to allow export of the viral RNA from the nucleus to the cytoplasm, where it serves as the mRNA for expression of Gag and Pol proteins, and as the genomic RNA that is packaged into new virions. Rev- mutants accumulate unspliced and partially spliced viral mRNAs in the nucleus (Nasioulas et al., 1995). Simple ("S-type") retroviruses (Nasioulas et al., 1995) such as ALV, lack Rev and RRE, but facilitate nuclear export of viral transcripts by use of a CTE. The CTEs of MPMV and SRV-1 have been shown to complement Rev- RRE- mutants of HIV-1 and SIV (Bray et al., 1994 and Zolotukin et al., 1994). Rous Sarcoma Virus (RSV) has been shown to contain a CTE or CTE-like sequence that promotes Rev-independent expression of HIV-1 Gag proteins (Ogert et al., 1996). The RSV CTE has been mapped to the 3' UTR, between nucleotides 8770 and 8925 and includes one copy of the direct repeat (DR) sequence flanking the RSV src gene. Thus CTEs are characterized by a combination of nucleotide sequence, location, secondary structure, and function, particularly the ability to complement Rev- RRE- mutants of complex retroviruses.

U.S. Pat. No. 5,880,276 describes a method for identifying (and making) a CTE (see Example 8). Such a method may be used to identify a CTE for use in the present embodiments. An adaptation of such a method comprises:

(1) Isolating a retroviral genomic sequence or cellular genomic sequence that shows homology with a known CTE (i.e., that is substantially similar, e.g., has 50% identity with a known CTE when compared using blastn at default perameters) Such a known CTE could, for example, be a CTE from an ASLV virus, from SRV-1, from MPMV, or from RSV, or could be any CTE or CTE-like sequence characterized by being found in the 3' UTR of a retrovirus genome between the env gene and the 3' LTR, that functions to mediate nuclear export of RNA in simple retroviruses;

(2) Insertion of such a sequence into a vector in cis, to produce a vector that is transcribed into mRNA, which is either differentially spliced, alternatively spliced, incompletely spliced or unspliced, and thus, not normally transported from the nucleous to the cytoplasm;

(3) Introduction of such a recombinant vector into mammalian cells;

(4) Assaying the cultured cells for expression of the DNA molecule such as by detection of its mRNA in the cytoplasm or production of protein encoded by the DNA molecule, wherein detection of such expression indicates that the sequence comprises a CTE; and (5) Isolation and purification of the sequence from the recombinant vector using standard methods.

CTE-like sequence refers to a sequence having the function of a CTE.

A virus is said to be replication competent in a particular cell line or cell type if that virus, without the need for a helper virus, can successfully undergo a complete replication cycle in the cell by infecting the cell, replicating and assembling in the cell and producing infectious progeny viruses.

Long Terminal Repeat (LTR) refers to terminal duplications produced when viral RNA is reverse-transcribed into DNA. These duplicated sequences are present at both ends of an integrated retrovirus genome (provirus), but are found as single copies in the retroviral RNA genome. LTRs are generated during the process prior to integration and consist of three structural regions:U3, R and U5. The LTR generally contains an enhancer sequence(s), promoter sequence(s), 3' RNA processing sequence(s), and integration (att) sequence (s). In a replication competent retrovirus, the LTR may also contain an active RNA polymerase II promoter which allows transcription of the integrated provirus by host cell RNA polymerase II to generate new copies of the retroviral RNA genome. Examples of LTRs include the LTR of HIV1 (Patricia, R., et al., AIDS Res. Hum. Retroviruses 3(1):41–55, 1987); the LTR of Mouse Mammary Tumor Virus (Lee, W., et al., Virology 159(1):39–48, 1987); and the LTR of Rous Sarcoma Virus (Yamamoto, T., et al., Cell 22(3):787–97, 1980).

Direct repeat (DR) sequences are identical or nearly identical sequences of DNA present as two or more copies in the same orientation in the same molecule. Such sequences need not be adjacent.

An amphotrophic virus is one that can replicate both in cells of its native host and also in cells of other species.

As used in this specification, complementarity refers to functional complementarity. A nucleotide sequence is complementary to another when it performs a similar function to the sequence to which it is complementary e.g., the LTR of MLV is complementary to the CTE of ASLV because when the CTE is removed from ASLV and replaced with a sequence from the MLV LTR, the resulting virus is replication competent in a host cell. It does not have to confer replication competence in the same cell type to be complementary, but merely confer replication competence in some cell type.

A second virus is said to be derived from a first virus if the second virus genome is substantially similar to the first virus genome, with the second virus retaining the majority of structural genes of the first, and preferably retaining 70%, 80%, 90% or 95% of the genome of the first virus.

An isolated nucleic acid has been substantially separated or purified away from other nucleic acid sequences in the cell of the organism in which the nucleic acid naturally occurs, i.e., other chromosomal and extrachromosomal DNA and RNA. The term isolated thus encompasses nucleic acids purified by standard nucleic acid purification methods. The term also embraces nucleic acids prepared by recombinant expression in a host cell as well as chemically synthesized nucleic acids. The nucleic acids of the present invention comprise at least a minimum length able to hybridize specifically with a target nucleic acid (or a sequence complementary thereto) under stringent conditions as defined below. The length of a nucleic acid of the present invention is preferably 15 nucleotides or greater in length, although a shorter nucleic acid may be employed as a probe or primer if it is shown to specifically hybridize under stringent conditions with a target nucleic acid by methods well known in the art. The phrase a peptide of the present invention means a peptide encoded by a nucleic acid molecule as defined in this paragraph.

The term complement, when used in the context of a nucleic acid sequence (e.g., ". . . the complement of the sequence shown in FIG. 1"), refers to the anti-paralell "mirror-image" sequence of a given sequences, such that, for DNA, A bonds with T, and G bonds with C.

A genetic fragment refers to any polynucleotide, DNA or RNA, derived from a larger polynucleotide.

A probe comprises an isolated nucleic acid attached to a detectable label or reporter molecule. Typical labels include radioactive isotopes, ligands, chemiluminescent agents, and enzymes. Primers are short nucleic acids, preferably DNA oligonucleotides 15 nucleotides or more in length, which are annealed to a complementary target DNA strand by nucleic acid hybridization to form a hybrid between the primer and the target DNA strand, then extended along the target DNA strand by a DNA polymerase enzyme. Primer pairs can be used for amplification of a nucleic acid sequence, e.g., by the polymerase chain reaction (PCR) or other nucleic-acid amplification methods known in the art. Probes and primers as used in the present invention preferably comprise at least 15 nucleotides of the nucleic acid sequences that are shown to encode specific proteins. In order to enhance specificity, longer probes and primers may also be employed, such as probes and primers that comprise 20, 30, 40, 50, 60, 70, 80, 90 or 100 consecutive nucleotides of the disclosed nucleic acid sequences. Methods for preparing and using probes and primers are described in the references, for example Sambrook et al., (1989) Molecular Cloning:A Laboratory Manual, Cold Spring Harbor, N.Y.; Ausubel et al., (1987) Current Protocols in Molecular Biology, Greene Publ. Assoc. & Wiley-Intersciences; Innis et al., (1990) PCR Protocols, A Guide to Methods and Applications, Innis et al. (Eds.), Academic Press, San Diego, CA. PCR primer pairs can be derived from a known sequence, for example, by using computer programs intended for that purpose such as Primer (Version 0.5, 1991, Whitehead Institute for Biomedical Research, Cambridge, Mass.).

Target Nucleic Acid as used in the specification refers to a nucleic acid that hybridizes with a probe. The conditions under which hybridization occurs may vary with the size and sequence of the probe and the target sequence.

By way of illustration only, a hybridization experiment may be performed by hybridization of a DNA probe (for example, a probe derived from the LTR of MLV labeled with a radioactive isotope) to a target DNA molecule which has been electrophoresed in an agarose gel and transferred to a nitrocellulose membrane by Southern blotting (a technique well known in the art and described in Sambrook et al., 1989).

Hybridization with a radio-labeled probe is generally carried out in a solution of high ionic strength such as 6×SSC at a temperature that is 20° C.–250° C. below the melting temperature, $T_m$, described below. For such Southern hybridization experiments where the target DNA molecule on the Southern blot contains 10 ng of DNA or more, hybridization is typically carried out for 6–8 hours using 1–2 ng/ml radiolabeled probe. Following hybridization, the nitrocellulose filter is washed to remove background hybridization. The wash conditions should be fairly stringent to remove background hybridization but to retain a specific hybridization signal. The Tm is the temperature (under defined ionic strength and pH) at which 50% of the target sequence hybridizes to a perfectly matched probe. The $T_m$ of such a hybrid molecule may be estimated from the following equation:

$$T_m=81.50° C.-16.6(\log_{10}[Na^+])+0.41(\% G+C)-0.63(\% \text{formamide})-(600/l)$$

Where l=the length of the hybrid in base pairs. This equation is valid for concentrations of $Na^+$ in the range of 0.01M to 0.4M, and it is less accurate for calculations of $T_m$ in solutions of higher $[Na^+]$. The equation is primarily valid for DNAs whose G+C content is in the range of 30% to 75%, and applies to hybrids greater than about 100 nucleotides in length (the behavior of oligonucleotide probes is described in detail in Ch. 11 of Sambrook et al., 1989). In the present case, the equation can reasonably be applied to a probe of about 96 nucleotides in length.

In general, high stringency wash conditions are used that include a temperature approximately 12–20° C. below the calculated $T_m$ of the hybrid pair under study. Exemplary hybridization conditions include wash conditions at a temperature of, for example, 48° C., 58° C., 62° C. or 68° C., with between 2× and 0.1×SSC and about 0.5% SDS, for instance, 62° C. with 0.1×SSC and 0.5% SDS. Exact experimental hybridization conditions are generally determined empirically in preliminary experiments in which samples of genomic DNA immobilized on filters are hybridized to the probe of interest and then washed under conditions of different stringencies. Such experimentation is routine, is well known and is described in detail in Sambrook et al, 1998, pages 9.47 to 9.55.

The above example is given entirely by way of theoretical illustration. One skilled in the art will appreciate that other hybridization techniques may be utilized and that variations in experimental conditions will necessitate alternative calculations for stringency.

A first nucleic acid is substantially similar to (or shows substantial similarity with) a second nucleic acid if, when optimally aligned (with appropriate nucleotide insertions or deletions) with the other nucleic acid (or its complementary strand), there is nucleotide sequence identity in at least about 50%, 60%, 70%, 80% or 90 to 95% of the nucleotide bases. Sequence similarity can be determined by comparing the nucleotide sequences of two nucleic acids using the BLAST sequence analysis software, for instance, the NCBI BLAST 2.0 program gapped blastn set to default parameters. (One example of such default settings would bet expect=10, filter=default, descriptions=500 pairwise, alignments=500, alignment view=standard, gap existence cost=11, per residue existence=1, per residue gap cost=0.85). This software is available from The National Center for Biotechnology Information (National Library of Medicine, Building 38A, Room 8N805, Bethesda, Md. 20894).

A portion (of a nucleotide sequence) as used in the specification refers to at least 10, or 20, 30 or 40 nucleotides, in some cases, it would be advantageous to use a portion comprising 50 or more contiguous nucleotides of that specified nucleotide sequence (but no more than about a kilobase). A portion as used herein may include a whole gene or a whole specified sequence, e.g., a portion of the DNA sequence of gene A may include as few as 10 nucleotides, or as many as 50 nucleotides or more, or the whole open reading frame or the entire gene, so long as the sequence comprises at least 10 nucleotides of the DNA sequence of gene A. A portion of the LTR of MLV may include the full 614 bp sequence, or as few as 10 nucleotides.

A first nucleic acid sequence is operably linked with a second nucleic acid sequence when the first nucleic acid sequence is placed in a functional relationship with the nucleic acid sequence. For instance, a promoter is operably linked to a coding sequence if the promoter affects the transcription or expression of the coding sequence.

Generally, operably linked DNA sequences are contiguous and, where necessary to join two protein coding regions, in the same reading frame.

A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques such as those described in Sambrook et al., (1989).

When referring to a probe or primer, the term specific for (a target sequence) indicates that the probe or primer hybridizes under stringent conditions substantially only to the target sequence in a given sample comprising the target sequence.

A purified peptide is a peptide that has been extracted from the cellular environment and separated from substantially all other cellular peptides. As used herein, the term peptide includes peptides, polypeptides and proteins. In preferred embodiments, a purified peptide is a preparation in which the subject peptide comprises 80% or more of the protein content of the preparation.

B. CELLS, VECTORS, CLONING AND EXPRESSION OF RECOMBINANT VECTORS IN HOST CELLS

The present invention utilizes standard laboratory practices for the cloning, manipulation and sequencing of nucleic acids, purification and analysis of proteins and other molecular biological and biochemical techniques, unless otherwise stipulated. Such techniques are explained in detail in standard laboratory manuals such as Sambrook et al. (1989) and Ausubel et al. (1987).

Chick Embryo Fibroblast (CEF) cells are generally used as host cells to grow avian-derived retroviruses (Petropoulos et al. 1991) and can be passaged up to about 30 times. Other suitable host cells include any avian derived cells such as QT6, a chemically transformed quail fibroblast cell line (Moscovici et al. 1977) or DF-1, a continuous non-transformed chicken cell line (Schaefner-Klein et al., in press, 1998).

The 293R cells are Puromycin resistant human kidney cells that express the Tva receptor, and were obtained from Dr. John A. T. Young of Harvard University. The 293R cells were generated as follows:293 cells (ATCC CRL-1573) were transfected by the calcium phosphate method (Wigler et al., 1979) with 20 micrograms of plasmid pKZ261 [a pCB6 expression plasmid encoding a synthetic Tva gene (Belanger et al., 1995)] and with 2 micrograms of plasmid pPur encoding puromycin-N-acetyl-transferase (Clonetech). The transfected cells were selected after 24 hours with medium containing 0.5 micrograms/ml puromycin. The 293R clone is one of a number of clones that express Tva and are susceptible to infection by ALV-A vectors.

An avian virus is rendered replication-defective by deleting all or part of the viral CTE. The avian virus used in this instance was derived from Avian Sarcoma Leukemia Virus (ASLV), but any simple avian retrovirus with a CTE may be used such as Rous Sarcoma Virus (RSV) (Federspiel et al, 1997) or any virus derived from RSV. The CTE-deleted vector will not replicate in CEF cells. The vector is linearized by restriction at a unique site and the ends of the linearized DNA are blunted with T4 DNA polymerase and dephosphorylated using standard techniques.

A molecular clone of a mammalian retrovirus is digested into small, blunt-end fragments, which are then ligated at specific restriction sites into the genome of the replication-defective avian retrovirus vector. The mammalian virus used in this particular instance was MLV, but any other mammalian retrovirus having a CTE-like sequence, such as MPMV, may be used.

The ligation product is used to transform *E. coli* cells. The recombinant plasmid is maintained in the bacterial cell and is expressed. Integration into the bacterial genome does not occur. Plasmid DNA containing the recombinant virus is isolated from the transformed bacteria and transfected into avian cells such as CEF cells.

To detect virus production, cell-free supernatants from successive passages of avian cells are monitored for reverse transcriptase activity and supernatants containing infectious virus are used to infect CEF or DF-1 cells. The region of virus containing the inserted DNA is amplified by PCR and sequenced using standard methods (Sambrook et al. 1989).

To determine replication competence, vectors are transfected into selected cell types such as mammalian and avian host cells. Viral expression is measured by assaying the supernatant of the cell growth medium for reverse transcriptase as described herein.

Any cell may be used as a potential host cell for the recombinant vector, depending on the CTE-like sequence chosen by the operator. Mammalian cells include HeLa cells, SW-527 human cells (ATCC deposit #7940), WISH cells (ATCC deposit #CCL-25), Daudi calls (ATCC deposit #CCL-213), Mandin-Darby bovine kidney cells (ATCC deposit #CCL-22) and Chinese Hamster ovary cells (ATCC deposit #CRL-2092). Avian cells that may be used include CEF cells, DF-1 cells and QT-6 cells (ATCC deposit #CRL-1708), chicken bursa lymphoblast cells (ATCC deposit #CRL-2112 and 2111), turkey cells (ATCC deposit #CRL-1835), duck cells (ATCC deposit #CCL-141) as well as any cultured, transformed or non-transformed avian cell, such as chicken fibroblast cells, chicken liver cells or chicken epidermal cells. Cells from other species may also be used. For instance, yeast cells that may be used include *Pichia pastoris* (ATCC deposit #201178) and *Saccharomyces cerevisiae* (ATCC deposit #46024). Insect cells include cells from *Drosophila melanogaster* (ATCC deposit #CRL-10191), the cotton bollworm (ATCC deposit #CRL-9281) and from *Trichoplusia ni* egg cell homoflagelates. Fish cells that may be used include those from rainbow trout (ATCC deposit #CLL-55), salmon (ATCC deposit #CRL-1681) and Zebrafish (ATCC deposit #CRL-2147). Amphibian cells that may be used include those of the Bullfrog, *Rana catesbelana* (ATCC deposit #CLL41). Reptile cells that may be used include those from Russell's Viper (ATCC deposit #CCL-140). Plant cells that could be used include Chlamydomonas cells (ATCC deposit #30485), Arabidopsis (ATCC deposit #54069) cells and tomato plant cells (ATCC deposit #54003).

PCR may be used to amplify the DNA sequences cloned into the Cla I site of the replicating virus, for instance, the following primers may be used:

5'-GAGCTGACTCTGCTGGTGCC-3' (SEQ ID NO:6) and

5'-CCCCCTCCCTATGCAAAAGCG-5' (SEQ ID NO:7). These primers anneal to the RSV sequence on either side of the Cla I site.

PCR may also be used to detect viruses harboring specific nucleic acid inserts. To detect a virus harboring the 96 bp fragment the following primers may be used:

5'-ATGTTTCCAGGGTGCCCCAA-3' (SEQ ID NO:4) and

5'-AGCAGAAGCGCGCGAACAGAA-3' (SEQ ID NO:5). To detect a virus harboring the 220 bp fragment, the following primers may be used:

5'-AGCTGAATATGGGCCAAACA-3' (SEQ ID NO:8) and

5'-TCGGGGAGCAGAAGCGCGCG-3' (SEQ ID NO:9).

Recombinant vectors selected by virtue of replication competence may be analyzed to determine the position and sequence of the inserted polynucleotide. For instance, sequencing may be performed by using a two-temperature thermal-cycle method in which the radiolabeling and termination reactions occur simultaneously. A reaction mixture containing 50 mM Tris-Cl (pH8.3), 50 mM Kci, 7 mM $MgCl_2$, 100 mM-mercaptoethanol, 170 $\mu$g of bovine serum albumin per ml, 0.25 pmol of primer, 2.5 $\mu$M deoxynucleoside triphosphates (dNTPs), 0.5 $\mu$Ci of [-$^{32}$P]dATP (800Ci/mmol), 1 U of Taq polymerase, and 8% dimethyl sulfoxide is prepared. The reaction mixture is divided into four separate tubes, each containing 1 $\mu$L of the appropriate ddNTP (ddA at 2.5 mM, ddC at 2.5 mM, ddG at 0.25 mM, and ddT at 5.0 mM). The reaction mixtures are overlaid with paraffin oil, placed in an UNO THERMOCYCLER™ (BIOMETRA INC.™, Tampa, Fla.) and heated at 95° C. for 5 min. The mixtures are then subjected to 25 cycles of 90° C. for 40 s and 62° for 80 s. Fifty percent formamide loading dye is added to the reaction mixtures, and the samples are fractionated on a 6% polyacrylamide-urea sequencing gel. The gel is then autoradiographed overnight, and the X-ray film developed with a KODAK™ RP X-OMAT™ processor.

C. EMBODIMENTS

The present invention teaches a retroviral vector, derived from an avian retrovirus, from which the CTE has been wholly or partially removed so as to make the virus replication defective, and replaced with a nucleotide sequence from a non-avian virus that is functionally complementary to the removed CTE sequence, allowing the recombinant virus to be replication competent in at least one non-native cell type.

In one embodiment, the CTE from RCASBP(A) was deleted by restricting out a 70 bp sequence containing the direct repeat (DR) between the MluI-Bsu136 sites. A CTE-like sequence from the LTR of the mammalian virus MLV was obtained by restricting the MLV genome with AluI and by purifying the excised fragment by gel electrophosesis. Such fragments were then recovered from the gel in a purified state. The linear RCASBP(A) vector and MLV-derived fragment were then ligated together using T4 ligase enzyme.

In one embodiment, the MLV LTR-derived fragment was the 220 bp AluI fragment shown in FIG. 2 (SEQ ID NO:2).

Alternatively, the polynucleotide to be cloned into the vector may be synthesized using a commercial nucleotide synthesizer or created by PCR using appropriate flanking primers. For instance, the 96 bp fragment of FIG. 1 can be so synthesized.

It has been unexpectedly found that the 220 bp LTR-derived AluI fragment (FIG. 2), when inserted into the ClaI site of RCASBP(A) predictably evolves through serial passages to produce a smaller fragment of 96 bp (FIG. 1; SEQ ID NO:1). Other embodiments, therefore, may include using fragments of various sizes from the LTR of a mammalian virus such as MLV, wherein such inserts predictably evolve to produce the 96 bp fragment. The size of such fragments is limited only by the size of the LTR in question. For instance, the entire LTR of MLV, which is about 614 bp long, may be used.

The 96 bp fragment corresponds to a part of the U3 region of the MLV LTR, upstream of the "TATA" box. The U3 region is a part of the LTR found upstream of the transcription start site that contains the majority of cis-acting control elements that regulate transcription initiation by cellular RNA polymerase II. The U3, R and U5 regions of the 3' LTR contain the cis-acting control elements involved in post transcriptional RNA processing of the 3' end of the RNA product. In one embodiment, the whole 614 bp LTR fragment, spanning the U3, R and U5 regions may be used. In another embodiment, the invention may use, as the inserted DNA, a fragment from the U3 region of a mammalian retrovirus (although a retrovirus native to any species may be used). For instance, the 489 bp U3 region of MLV may be used.

Alternately, only a portion of the CTE need be deleted from the avian genome, and replaced with a CTE-like sequence, or with a portion of a CTE-like sequence, from a retrovirus of another species.

In one embodiment, the retroviral vector was derived from an Avian Sarcoma Leukemia Virus (ASLV), from which the CTE had been wholly or partially removed and replaced with a nucleotide sequence derived from an amphotrophic MLV. In this embodiment, the MLV-derived sequence comprised the LTR sequence of FIG. 3.

In another such embodiment, the CTE was replaced (wholly or partially) with a nucleotide sequence having at least a 75% or at least 80, 85, 90 or 95% identity with the nucleotide sequence shown in FIG. 3 (SEQ ID NO:3). In an alternative embodiment, the CTE may be replaced (wholly or partially) with a nucleotide sequence comprising at least about 50 contiguous nucleotides, or 75, 100, 125, 150, 175 or 200 contiguous nucleotides wherein said sequence shows at least a 75% or at least 80, 85, 90 or 95% identity with the sequence of FIG. 3 (SEQ ID NO:3).

In another such embodiment, the CTE may be replaced (wholly or partially) with a nucleotide sequence having substantial similarity (as defined herein) with the nucleotide sequence shown in FIG. 3. In another such embodiment, the CTE may be replaced with a nucleotide sequence comprising at least about 15 contiguous nucleotides (or at least about 30, 50, 100, 200, 400 or 614 contiguous nucleotides) from the LTR of MLV.

In every case, the inserted sequence is a sequence that functionally complements the lost CTE function by restoring replication competence in at least one non-native cell type. The inserted CTE-like sequence may be an LTR or part of an LTR and may consist of one or more direct repeats from the LTR.

In one particular embodiment, the avian virus may be derived from an ASLV virus, wherein the CTE has been wholly or partially replaced with any mammalian nucleotide sequence from an amphotrophic virus that functions as a CTE, to produce a broad host-range vector that is competent in both avian and mammalian cells.

In another embodiment, the avian virus used may be Rous Sarcoma Virus (RSV). RSV is known to possess a CTE in its 3' untranslated region that has been shown to promote Rev-independent expression of HIV-1 Gag proteins (Ogert et al., 1996). This CTE is found between nucleotides 8770 and 8925 in the RSV genome and includes one copy of the direct repeat (DR) flanking the RSV src gene. In RSV, removal of both DRs is required to make RSV replication defective, and in one embodiment, both DRs of RSV (or an RSV derived virus) may be deleted prior to ligating in a heterologous CTE-like sequence.

The present invention may also be practiced by inactivating the avian CTE, for instance by using standard techniques for site-directed mutagenesis (Sambrook at al. 1989, chapter 15), and by then inserting into the avian genome a sequence that performs essentially the same function as the CTE making the recombinant virus replication competent in at least one non-native cell type. Site directed mutagenesis may be done, for instance, by the techniques of linker-insertion, generation of nested sets of deletion mutants or cleavage of double-stranded closed circular DNA with panceratic DNAase I (Sambrook at al. 1989, chapter 15). The CTE-like sequence may be derived from the LTR of a mammalian retrovirus, such as MLV, for instance from the LTR of MLV, for instance, the 96 bp or the 220 bp sequence as set out in this specification (SEQ ID NO:1 and SEQ ID NO:2). Such a construct produces a broad host-range retroviral vector capable of replicating in both avian and mammalian cells.

Non-site directed mutagenesis may be used to inactivate the CTE, such as transposon mutagenesis using Tn5. This would be useful for detection and functional deletion of CTE-like sequences that lack the general characteristics of the currently characterized CTEs.

The present invention may also be practiced by leaving in the avian CTE sequence and simply ligating in a sequence derived from a mammalian retrovirus, such as sequence from MLV for instance from the MLV LTR, such as the sequence of FIG. 3 or a sequence showing substantial similarity to the sequence of FIG. 3 (SEQ ID NO:3).

The present invention also provides a method for making a broad host-range retroviral vector derived from an avian retroviral vector by providing an avian retroviral vector and partially or wholly removing the CTE and replacing it with a fragment from a mammalian retroviral vector that performs essentially the function of a CTE. Alternately, the avian CTE may be left in and a mammalian fragment may be ligated into the genome. Such a fragment may be ligated in close to the CTE, for instance, within 300 bp or 150 bp of the CTE.

The present invention also provides a method for using such a vector both for research purposes and for clinical purposes, such as for the delivery of genetic elements into either mammalian or avian cells. The present invention teaches a method for delivering genetic information, such as information encoded in a nucleotide sequence, into a target cell. Such an embodiment uses the vector of the present invention, into which is inserted at the ClaI restriction site of the vector, a nucleotide sequence to be delivered to a target cell. The nucleotide sequence is delivered to the target cell by contacting the broad host-range vector with the target cell, without the need for a "helper" virus or special cell line, whereby nucleotides are transferred into the genome of the target cell. The viral construct becomes integrated into the target cell genome and the insert gene is expressed under the control of the viral promoter. This method may be useful for gene therapy applications and in research.

EXAMPLE 1

Cell Culture and Transfection

Chick Embryo Fibroblast (CEF) cells are non-transformed chicken fibroblast cells that may be passaged up to about 30 times. CEF cells were cultured from 11-day embryos of "line 0" chickens (Witcomb et al., 1995) and maintained in Dulbecco's modified Eagle's medium (DMEM; GIBCO, BRL™) supplemented with 5% fetal bovine serum (FBS), 5% newborn calf serum (NBS), 3% tryptose phosphate broth, 100 U of penicillin per ml and 100 $\mu$g of streptomycin per ml (Federspiel et al, 1997). DF-1 cells were cultured identically to CEF cells. The 293R cells, that stably express the avian subgroup A (Tva) receptor, were maintained in DMEM supplemented with 5% FBS, 5% NBS, and antibiotics. Cells were passaged using Trypsin-DeLarco medium (QUALITY BIOLOGICAL, INC.™, MD.)

Transfections were preformed by the calcium phosphate method (Wigler et al., 1979) using 10 to 20 $\mu$g of DNA per 100 mm dish.

EXAMPLE 2

Construction and Expression of RCASBP(A):220 bp Vector

The ALV-based vector, RCASBP (Hughes et al., 1990) was rendered replication-defective by deleting a 70 bp MluI-Bsu136 fragment containing the direct repeat (DR) from the CTE. This sequence is located between the envelope gene and the polypurine tract (ppt) and is required for normal viral growth (Sorge, Ricci and Hughes, 1983). The resulting plasmid (RCASBP DR) was linearized at the unique ClaI restriction site. The ends of the DNA were blunted with T4 DNA polymerase and dephosphorylated using shrimp alkaline phosphatase (BOEHRINGER™) (Sambrook et al., 1989).

Murine Leukemia Virus (MLV4070A) (Shinnick et al. 1981; Ott et al, 1992) was digested into small, blunt-end fragments, with the restriction enzyme AluI. These fragments, including the 220 bp fragment (FIG. 2; SEQ ID NO:2), were ligated into the ClaI site of the RCASBP DR vector.

The ligation mixture was used to transform *E. coli* DH5 (ATCC deposit #53868) cells (Sambrook et al., 1989). Plasmid DNA containing RCASBP DR with the MLV insert was isolated from the transformed DH5 cells by standard methods (Sambrook et al., 1989) and transfected into CEF and DF-1 avian cells.

EXAMPLE 3

Construction and Expression of RCASBP(A):96 bp Vector

The ALV-based vector, RCASBP was rendered replication-defective by deleting a 70 bp MluI-Bsu136 fragment containing the direct repeat (DR) from the CTE. The resulting plasmid (RCASBP DR) was linearized at the unique ClaI restriction site. The ends of the DNA were blunted with T4 DNA polymerase and dephosphorylated using shrimp alkaline phosphatase.

The 96 bp polynucleotide of FIG. 2 (SEQ ID NO:2) may be synthesized using a commercial nucleotide synthesizer or using PCR with appropriate flanking primers chosen using the sequence information in FIGS. 1 (SEQ ID NO:1) and 3 (SEQ ID NO:3). Such primers have the characteristics as explained herein under the definitions section. Such primers flank the sequence to be synthesized, one primer being complementary to the 3'–5' strand and the other primer being complementary to the 5'–3' strand, and should preferably be from about 12 to 30 nucleotides long. Examples of such primers are:

5'-ATGTTTCCAGGGTGCCCCAA-3' (SEQ ID NO:4) and

5'-AGCAGAAGCGCGCGAACAGAA-3' (SEQ ID NO:5).

The 96 bp fragment so constructed may then be ligated into the ClaI site of the RCASBP DR vector described above.

The ligation mixture may be used to transform *E. coli* DH5 cells. Plasmid DNA containing RCASBP DR with the MLV insert may be isolated from the transformed bacteria by standard methods and transfected into CEF and DF-1 cells.

EXAMPLE 4

Clone Selection

To detect virus production, cell-free supernatants from successive passages of CEF cells were monitored for reverse transcriptase activity which indicates that cells have been transformed and that the retroviral vector is replicating within the transformed cells (Whitcomb et al. 1995; Barsov and Hughes, 1996). One milliliter of culture supernatant was centrifuged in a refrigerated EPPENDORF™ tabletop centrifuge for 30 min at the maximum speed. Viral pellets were assayed for reverse transcriptase activity by measuring the incorporation of $[^{-32}P]dGTP$ into acid-precipitable material, using an oligo(dG) primer and a poly(rC) template (Petropoulous et al, 1991).

Supernatants containing infectious virus were used to infect CEF, DF-1 and 293R cells to make Hirt DNA (Hirt, 1967). The region of RCASBP containing the inserted MLV DNA was amplified by PCR from Hirt DNA and the amplification products were sequenced.

Alternately, PCR may be performed using crude cell lysates rather than using Hirt DNA, for instance, by the following protocol. Two microliters of the loose cell pellet is added to eight microlitres of a lysis buffer (1×PCR buffer with 0.1% Triton X-100). To disrupt the cells, the suspension is overlaid with 200 µl of paraffin oil and sonicated with a VIBRACELL™ sonicator (SONICS AND MATERIALS, INC.™, Danbury, Conn.) equipped with a microprobe at level 3 for 15 s. The emulsion is then centrifuged at the maximum speed in a refrigerated EPPENDORF™ tabletop centrifuge for 10 min to separate the phases, and 1.5 µl of the aqueous phase was used in the PCR reaction.

To amplify the DNA sequences cloned into the Cla I site of the replicating virus, the following primers were used:

5'-GAGCTGACTCTGCTGGTGCC-3' (SEQ ID NO:6) and 5'-CCCCCTCCCTATGCAAAAGCG-5' (SEQ ID NO:7). These primers anneal to the RSV sequence on either side of the Cla I site.

To detect viruses harboring the 96 bp insert (SEQ ID NO:1), the following primers may be used:

5'-ATGTTTCCAGGGTGCCCCAA-3' (SEQ ID NO:4) and 5'-AGCAGAAGCGCGCGAACAGAA-3' (SEQ ID NO:5). To detect viruses harboring the 220 bp fragment (SEQ ID NO:2), the following primers may be used:

5'-AGCTGAATATGGGCCAAACA-3' (SEQ ID NO:8) and

5'-TCGGGGAGCAGAAGCGCGCG-3' (SEQ ID NO:9).

Sequencing of the clones was done using an automatic cycle sequencing machine and a PRISM™ READY REACTION™ dideoxy cycle sequencing kit (Applied Biosystems, Foster City, Calif.). Sequencing reactions were analyzed with an automated 373A DNA sequencer (Applied Biosystems).

EXAMPLE 5

Expression of Vectors in Host Cells

Transfections into avian and mammalian cells were performed by the calcium phosphate method (Wigler et al., 1979) using 10 to 20 µg of DNA per 100 mm dish and using a glycerol shock 4 h after the precipitate was added. The transfected cells were passaged to confluence. Prior to passage, the culture supernatant was collected, cleared by centrifugation at 1500×g for 10 min and stored at −70° C. for later analysis.

Viral expression was measured by assaying the supernatant of the cell growth medium for reverse transcriptase as described herein. Results were analyzed semi-quantitatively by standard techniques to determine which viral constructs replicated in mammalian and/or avian cells.

The above embodiments are set out only as examples. The scope of the invention is to be interpreted only in view of the claims.

It should be apparent to one skilled in the art that the invention described herein can be modified in arrangement and detail without departing from the scope or spirit of the invention. We claim all such modifications.

REFERENCES

Ausubel et al., *Current Protocols in Molecular Biology*, 1987. Greene Publ. Assco. & Wiley-Intersciences.
Barber et al., U.S. Pat. No. 5,591,624.
Barber, et al., U.S. Pat. No. 5,716,832.
Barsov, E. V. and Hughes, S. A., *J. Virol.* 70:3922–3929, 1996.
Belanger et al., *J. Virol.* 69(2):1019–1024, 1995.
Bray et al., *Proc. Natl. Acad. Sci. USA* 91:1256–1260, 1994.
Burns, et al., U.S. Pat. No. 5,512,421.
Coffin, J., et al., eds. *Retroviruses*, 1997. Cold Spring Harbor Laboratory Press.
Federspiel, M., and Hughes, S. *Methods in Cell Biology: Methods in Muscle Biology*, 52: 179–214, Emerson and Sweeney, eds., Academic Press.
Hammarrsjold et al., U.S. Pat. No. 5,585,263.
Hughes, S. H., et al., *J. Reprod. Fert.*, Suppl. Vol. 41, pp. 39–49, 1990.
Hirt, B. *J. Mol. Biol.* 26:365, 1967.
Kriegler et al., U.S. Pat. No. 5,652,130.
Kriegler et al., U.S. Pat. No. 5,252,465.
Lee, W., et al., *Virology* 159(1):39–48, 1987
Moscovici et al, *Cell*, 11, 95–103, 1977.
Nasioulas, G. ; etal., *Proc. Natl. Acad. Sci.* (U.S.) Vol. 92, pp. 11940–11944, 1995.
Ogert, R. ; et al., *J. Virol*, 70 (6) p. 3834–3843, 1996.
Ottetal. *J. Virol*. 66(10):6107–6116, 1992.
Pasquinelli et al. *EMBO, J*, (England) 16 (24), p. 7500–10, 1997.
Patricia, R., et al., AIDS Res. Hum. Retroviruses 3(1) :41–55, 1987
Petropoulos, C. and Hughes, S. *J Virol*. 65 3728–3737, 1991.
Rizvi et al., Virology, (U.S.) 244 (2), pp. 517–32, 1996.
Sambrook et al., *Molecular Cloning: A Laboratory Manual*, 1989. Cold Spring Harbor Laboratory Press.
Schaefer-Klein, J., et al., *J. Virol*. 48:667–675, 1983.
Shinnick, T., Lerner, R. and Sutcliffe, J., *Nature* 239:543–548, 1981.
Whitcomb, J. M., Ortiz-Conde, B. A., Hughes, S. H., *J. Virol*. 69:6228–6238, 1995.
Wigler, M., et al., *Proc. Natl. Acad. Sci. U.S.A.* 76:1373–1376, 1979.
Yamamoto, T., et al., Cell 22(3):787–97, 1980.
Zolotukhin et al. *J. Virol*. 68 7944–7952, 1994.

What is claimed is:

1. A vector comprising an avian retrovirus, wherein a native CTE of the retovirus has been inactivated wherein all or a part of the CTE has been deleted, and into which has been inserted a nucleotide sequence comprising SEQ ID NO: 1, wherein the vector is replication competent in at least one cell type other than an avian retroviral host cell.

2. The vector of claim 1 wherein the nucleotide sequence comprises SEQ ID NO: 2.

3. The vector of claim 2 wherein the nucleotide sequence comprises SEQ ID NO: 3.

4. The vector of claim 1 wherein the avian retrovirus comprises Avian Sarcoma Leukosis Virus, Replication Competent Avian Leukosis Virus, or Rous Sarcoma virus.

5. The vector of claim 1 wherein the nucleotide sequence comprises a U3 region of a non-avian retroviral Long Terminal Repeat (LTR) of a non-avian retrovirus.

6. The vector of claim 1 wherein the vector is replication competent in both mammalian and avian cells.

7. The vector of claim 3 wherein the non-avian virus is murine leukemia virus (MLV).

8. A method of delivering nucleotides into a target cell comprising inserting a nucleotide sequence to be delivered into the vector of claim 1, and contacting the vector with at least one target cell, whereby the nucleotide sequence to be delivered is transferred from the vector into the target cell.

9. A method of making a vector that is replication competent in at least one non-native cell type comprising inactivating a CTE, wherein all or a part of a CTE sequence has been deleted from an avian-derived retrovirus and replacing the excised sequences with a a nucleotide sequence comprising the nucleotide sequence as set forth as SEQ ID NO:1, whereby the vector is replication competent in at least one cell type other than the avian retroviral host cell.

10. The vector of claim 1 wherein all or a portion of the CTE comprises a direct repeat (DR).

11. The vector of claim 5, wherein the non-avian virus is a mammalian retrovirus.

12. The vector of claim 1, wherein the inactive CTE was inactivated by ligation of the nucleotide sequence into the CTE.

13. The vector of claim 1, wherein the inactive CTE has been inactivated by site-directed mutagenesis.

* * * * *

UNITED STATES PATENT AND TRADEMARK OFFICE

CERTIFICATE OF CORRECTION

PATENT NO. : 6,492,166 B1 
DATED : December 10, 2002
INVENTOR(S) : Ferris et al.

It is certified that error appears in the above-identified patent and that said Letters Patent is hereby corrected as shown below:

Column 7,
Line 54, "20º C.-250º C." should be -- 20º C.-25º C. --.

Column 8,
Line 1, "81.50º C." should be -- 81.5º C. --.
Line 42, "bet" should be -- be: --.

Column 16,
Line 50, "Ottelal" should be -- Ott et al. --.

Column 20,
Line 53, "claim 3" should be -- claim 5 --.

Signed and Sealed this

Twenty-third Day of December, 2003

JAMES E. ROGAN
*Director of the United States Patent and Trademark Office*